United States Patent [19]
Marin et al.

[11] Patent Number: 5,827,310
[45] Date of Patent: Oct. 27, 1998

[54] APPARATUS FOR FORMING CUSTOM LENGTH GRAFTS AFTER ENDOLUMINAL INSERTION

[75] Inventors: Michael Marin; Ralph Marin, both of New York, N.Y.

[73] Assignee: Endovascular Systems, Inc., Cross River, N.Y.

[21] Appl. No.: 783,174

[22] Filed: Jan. 14, 1997

[51] Int. Cl.⁶ .................................................. A61B 17/22
[52] U.S. Cl. .......................................... 606/167; 606/159
[58] Field of Search .................................... 606/159, 167, 606/170, 194, 192, 198

[56] References Cited

U.S. PATENT DOCUMENTS

| | | | |
|---|---|---|---|
| 2,944,552 | 7/1960 | Cannon | 606/159 |
| 5,395,311 | 3/1995 | Andrews | 606/159 |
| 5,507,769 | 4/1996 | Marin et al. | |
| 5,628,746 | 5/1997 | Clayman | 606/194 |

OTHER PUBLICATIONS

Endovascular remote endarterectomy in femoropopliteal long segmental occlusive diease, F.L. Moll, et al., The Journal of Cardiovascular Surgery; vol. 37. Suppl. 1 to No. 3.

The Mollring Cutter Rmote Endarterectomy: Preliminary Experinece with a New Endovascular Technique for Treatment of Occlusive Superfical Femoral Artery Disease, Gwan H. Ho. et al., Journal Endovasc Surg. 1995: 2:278–287.

Endovascular Remote Endarterctomy in Femoropopliteal Occlusive Disease: One–year Clinical Experience with the Ring Strip Cutter Device, G. H. Ho. et al., 1996 W.B. Saunders Company Ltd., 1078–5884/96.

*Primary Examiner*—Michael Powell Buiz
*Assistant Examiner*—Kevin Truong
*Attorney, Agent, or Firm*—Darby & Darby

[57] ABSTRACT

A device for endoluminally cutting a graft is disclosed. The device includes an elongated catheter having an actuator at its proximal end and a cutting element remote from its proximal end. The actuator causes the cutting element to sever the graft endoluminally. The cutting element effects a cut through the wall of the graft to cut the graft, endoluminally, to a desired length. The cutting element includes a portion shaped so that the catheter can be positioned relative to the graft with the graft in close proximity to the cutting element.

15 Claims, 7 Drawing Sheets

FIG. 2
FIG. 4
FIG. 5
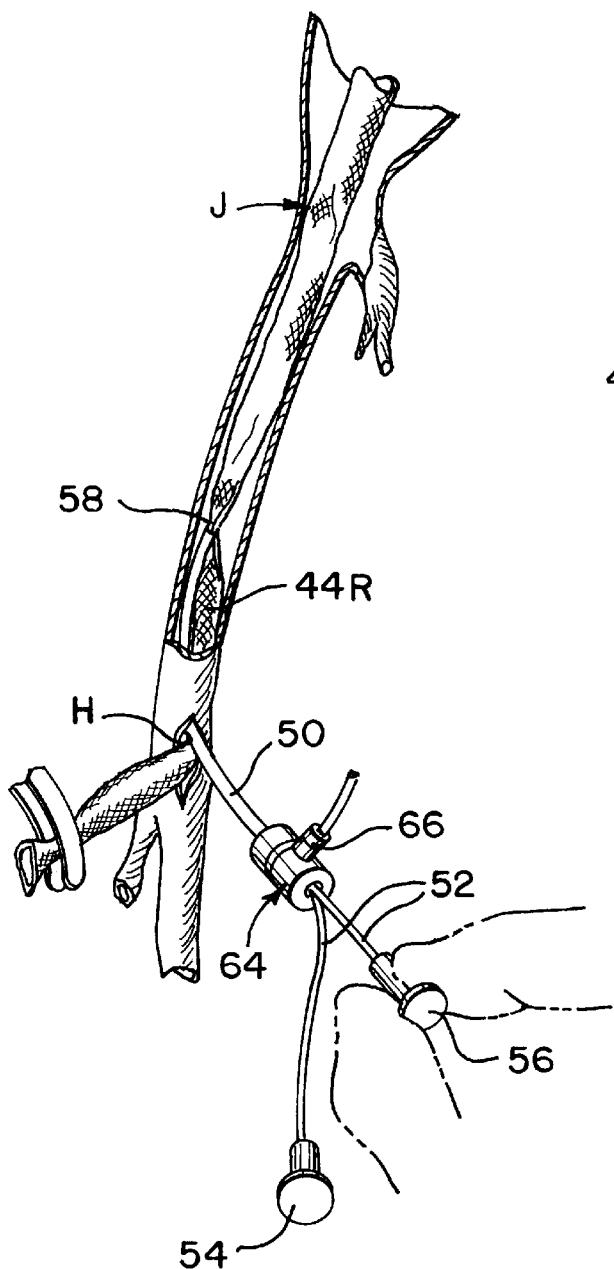
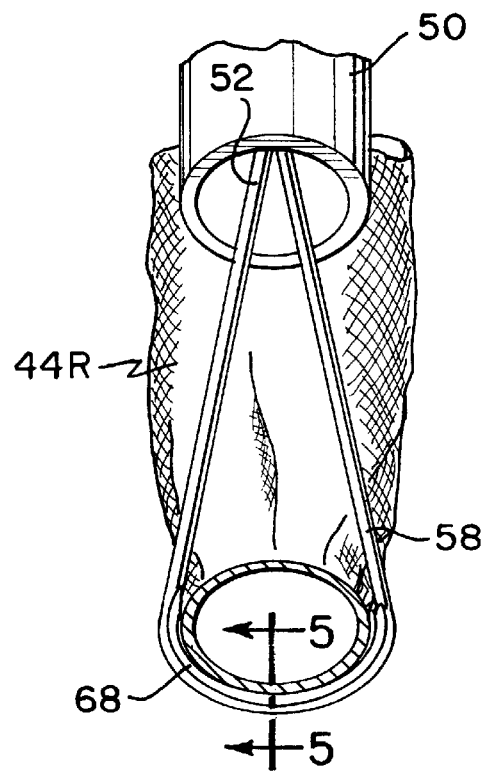
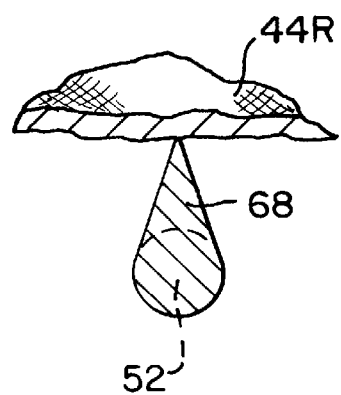

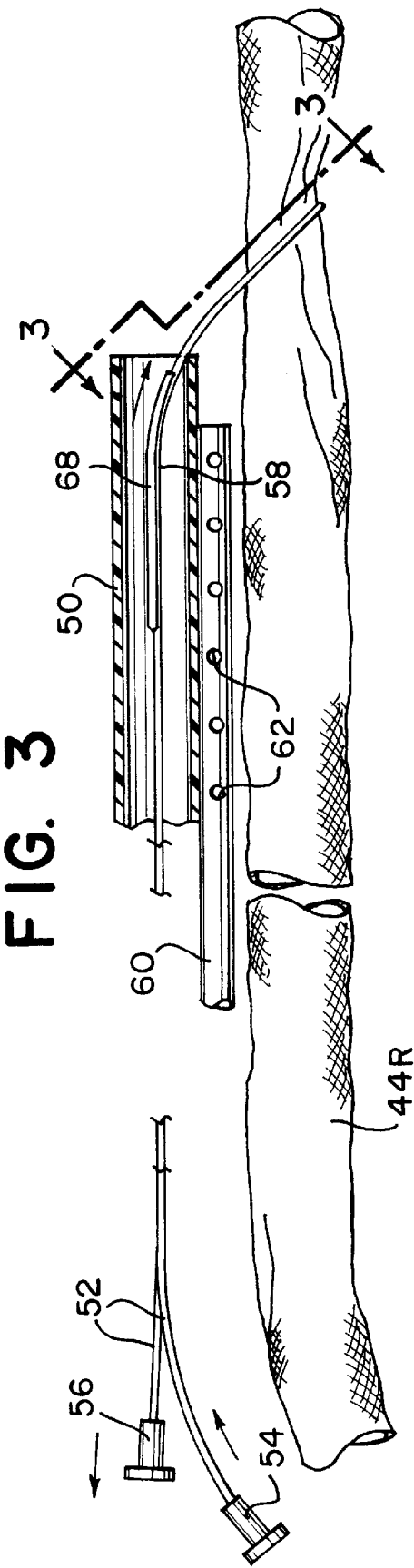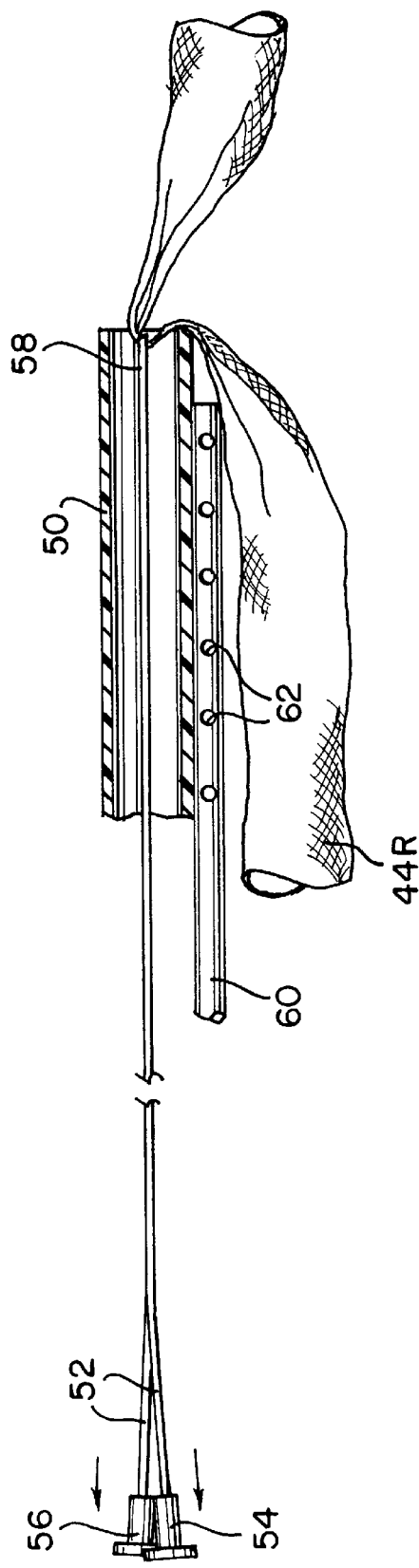

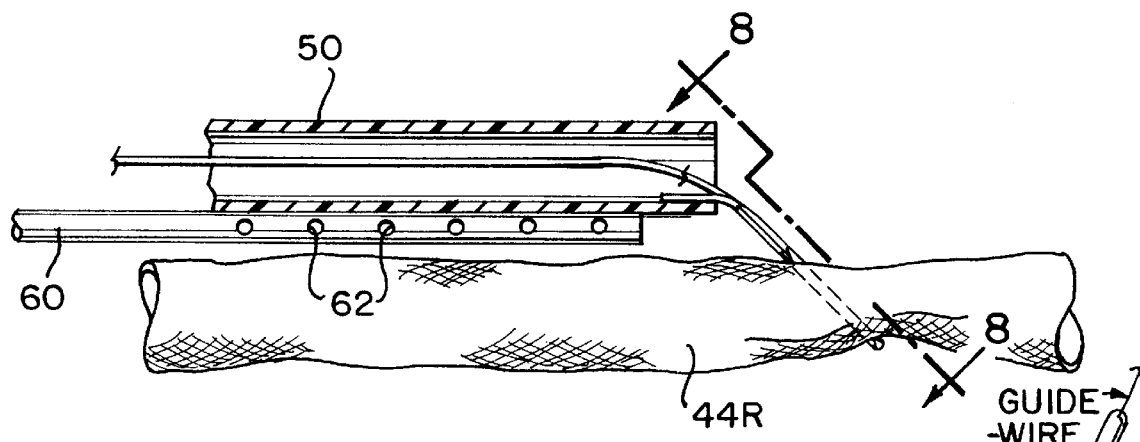
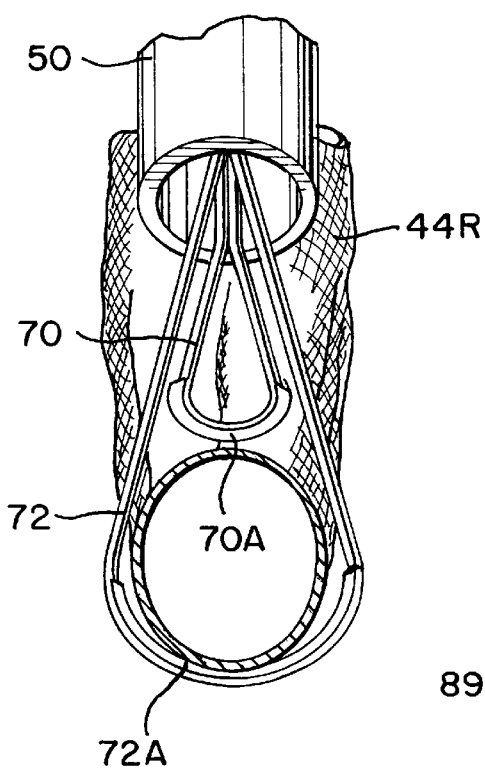
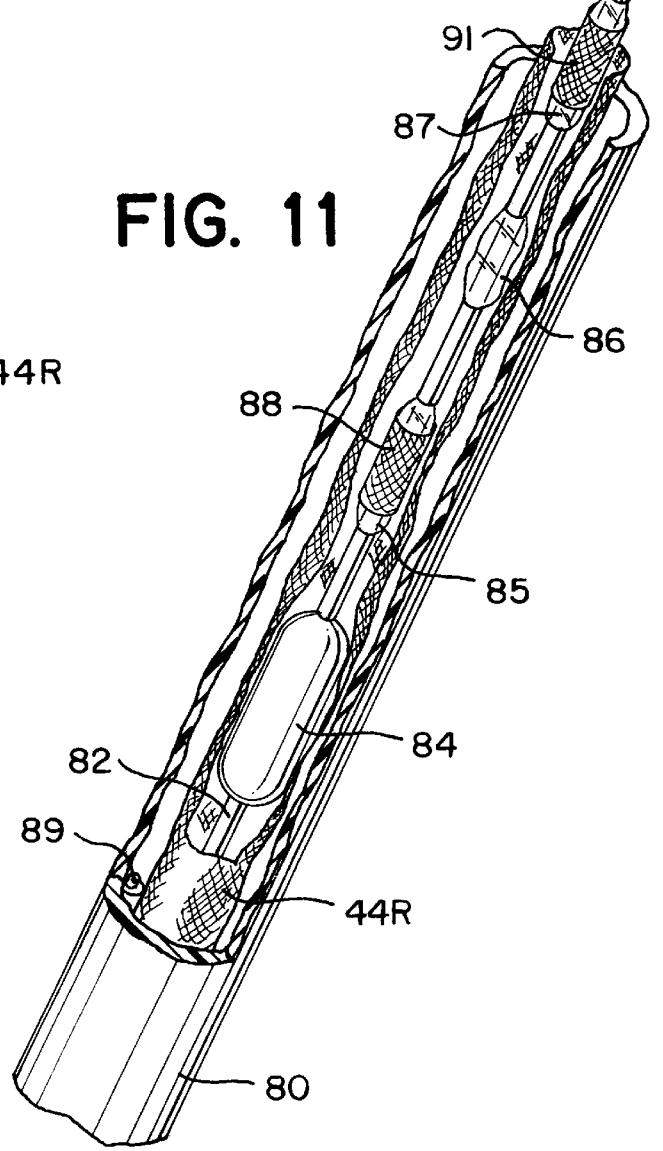

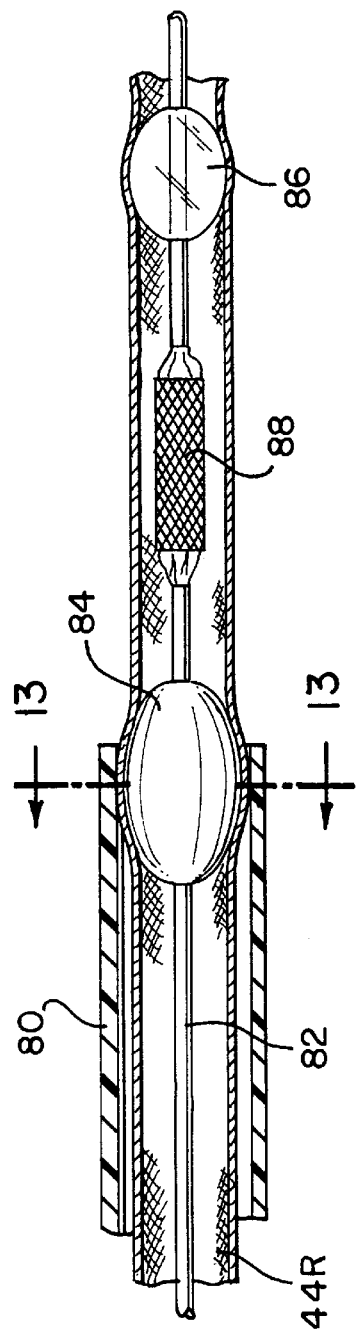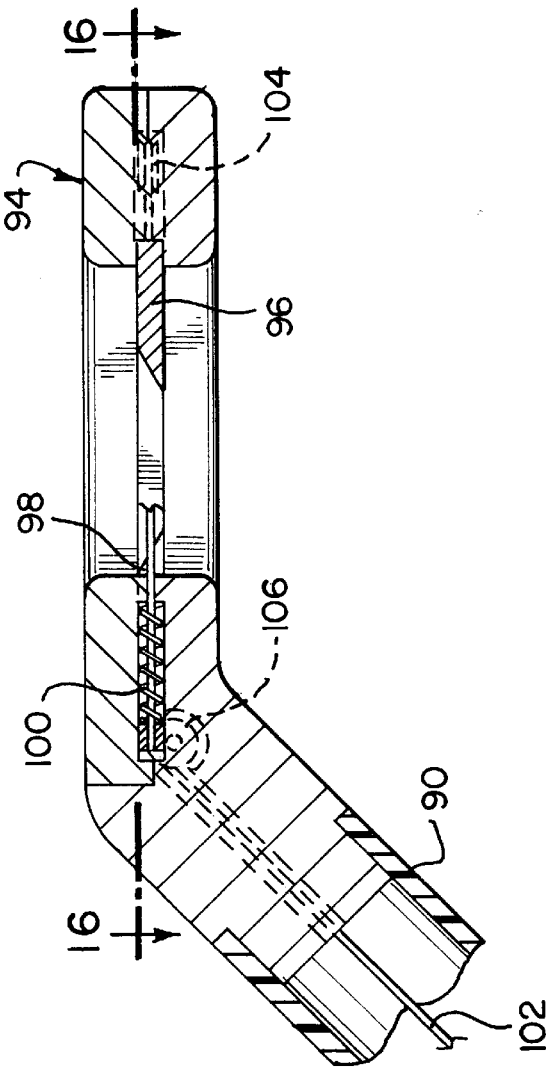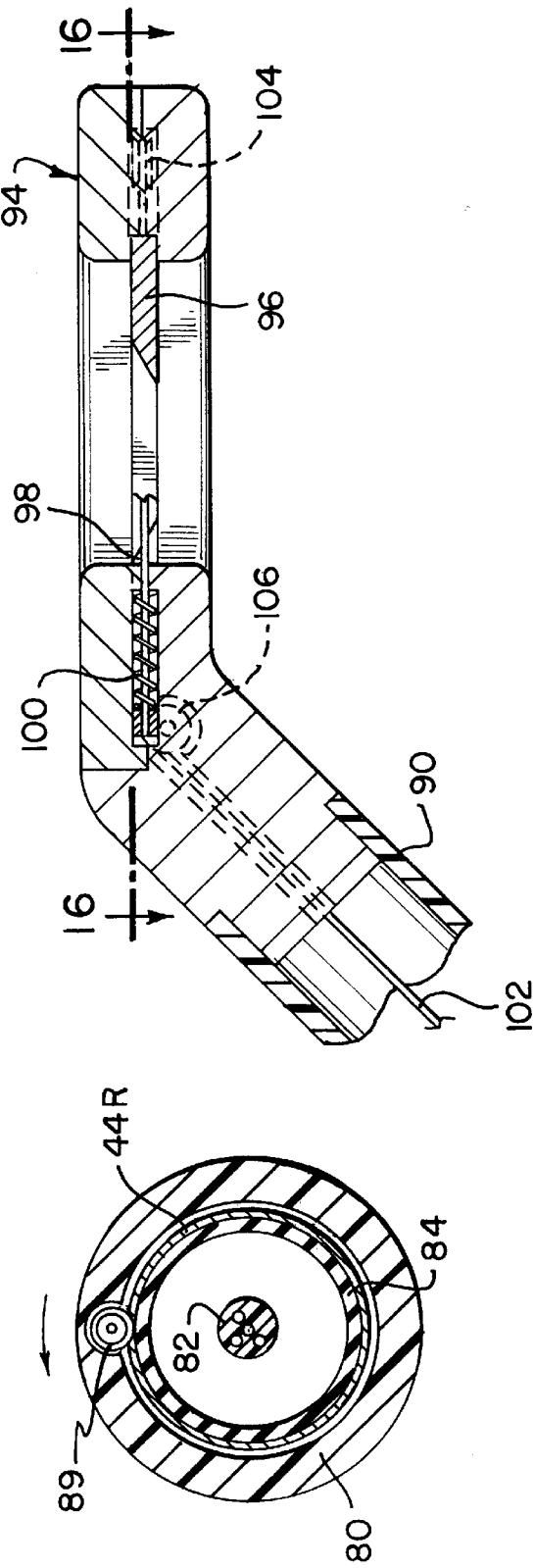

FIG. 16
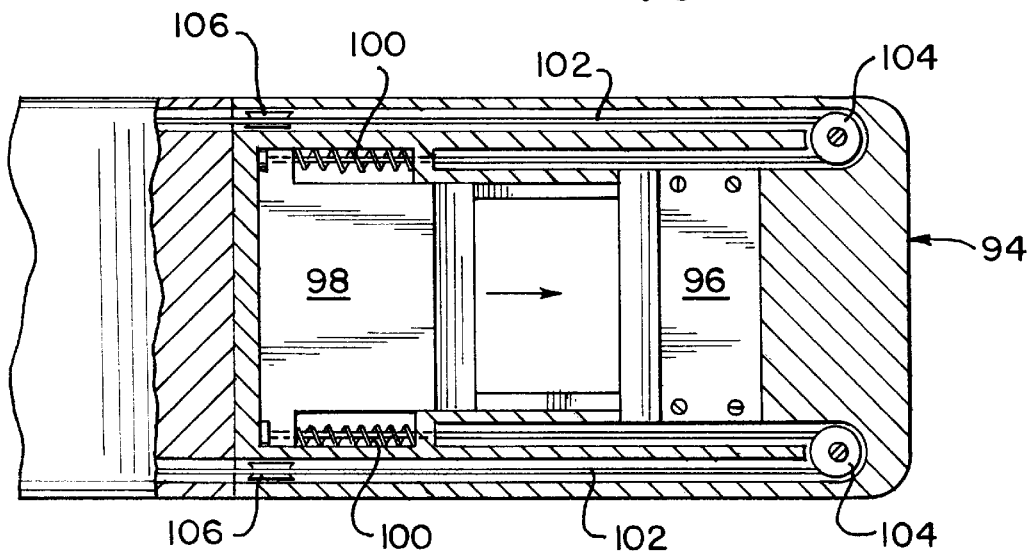
FIG. 17
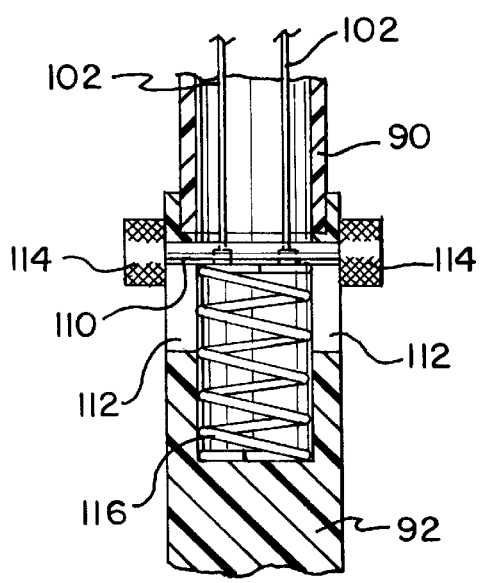
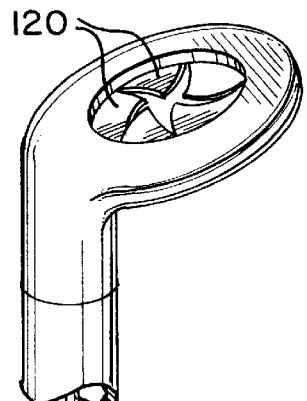
FIG. 18

APPARATUS FOR FORMING CUSTOM LENGTH GRAFTS AFTER ENDOLUMINAL INSERTION

FIELD OF THE INVENTION

This invention relates to a method for endoluminally deploying a graft in a body passageway, for example, for the purpose of isolating an abdominal aortic aneurysm.

BACKGROUND OF THE INVENTION

Marin et al. U.S. Pat. No. 5,507,769 describes a method and apparatus for endoluminally deploying a graft across an aortic aneurysm and associated common iliac aneurysms. In that patent, separate grafts are advanced through a patient's femoral and iliac arteries and aligned in a common region in the aorta above the aneurysm. Cephalic stents are deployed in that region to effectively create a bifurcated graft with the individual legs of the graft extending into the patient's arteries. Suitable stents are likewise deployed in these legs caudal of the aneurysm, thus isolating the aneurysm.

Marin et al. U.S. Pat. No. 5,507,769 in its entirety is hereby incorporated by reference.

The iliac arteries each include a branch known as the internal iliac artery. It is necessary that the grafts terminate cephalic of the internal iliac arteries so as not to block blood flow through these arteries. Assuming that the upper arteries may vary in length, the appropriate length of an individual graft will also need to vary considerably from patient to patient. This means that the surgeon must anticipate the length of the graft. If he/she is mistaken, the graft must be removed and a new graft inserted so as not to block important branch arteries, which is obviously undesirable. Moreover, the manufacturer must make different length grafts and the hospital must keep an inventory of all of the different lengths that may ultimately be needed.

OBJECT OF THE INVENTION

The object of the invention is to alleviate the foregoing problems.

More specifically, it is an object of the invention to provide a method for endoluminally placing a graft of a standard length in a body passageway wherein the final length of the graft may be formed endoluminally.

SUMMARY OF THE INVENTION

In accordance with the invention, a graft is inserted into a passageway such as a patient's artery. After the distal end of the graft is tacked to the passageway, a special intraluminal cutting device is threaded along the graft and actuated at the appropriate position so that the graft can be cut to the proper size.

The cutting device may be contained within the delivery system along with the graft such that actuation of a cutting element may take place entirely within the catheter system. This arrangement will permit this procedure to be performed percutaneously eliminating the need to directly expose the artery.

In a preferred embodiment, the cutting device may include a tube through which a contrast solution can be introduced into an artery so that the position of the cutting device can be precisely determined by an arteriogram. For example, in the case of an abdominal aneurysm, the cutting device will be positioned so that the proximal end of the graft will be severed at a point which is cephalad of the internal iliac artery.

IN THE DRAWINGS

FIG. 2 is a diagram showing how the invention is practiced;

FIG. 3 is a side view partially in section showing a first type of endovascular cutting device according to the invention;

FIG. 4 is a top perspective view of the cutting device shown in FIG. 3;

FIG. 5 is a sectional view along the line 5–5 of FIG. 4;

FIG. 6 is a side plan view partially in section showing how the cutting device of FIG. 3 operates;

FIG. 7 is a side view partially in section showing a second type of a cutting device which can be used in accordance with the invention;

FIG. 8 is a sectional view along the line 8—8 of FIG. 7;

FIG. 11 is a perspective view showing a fourth type of cutting device which can be used in accordance with the invention;

FIG. 12 is a side plan view partially in section showing the cutting device of FIG. 11 preparatory to cutting a graft;

FIG. 13 is a sectional view along the line 13—13 of FIG. 12;

FIG. 15 is a side sectional view of the cutting device shown in FIG. 14;

FIG. 16 is a sectional view along the line 16—16 of FIG. 15;

FIG. 17 is a sectional view along the line 17—17 of FIG. 14; and

FIG. 18 is a perspective view of a sixth type of cutting device which can be used in accordance with the invention.

DETAILED DESCRIPTION

The present invention was developed as an improvement over the endoluminal grafting procedure disclosed in U.S. Pat. No. 5,507,769 but the invention is not limited to that procedure. Just as in the case of U.S. Pat. No. 5,507,769, the invention may be used to bypass pathological defects other than aneurysms and vascular occlusions, for example malignancies. The invention is not limited to arteries or even the vascular system, and will have utility in other body passageways, such as the trachea, esophagus or colon, or wherever grafts have or may have utility. In general, the invention will have utility with any passageway (whether or not bifurcated) so long as the ability to customize the length of the graft in situ is beneficial. Nevertheless, despite the broad application of the basic principles of the invention, the preferred embodiment is described below in connection with the placement of a bifurcated graft for the purpose of bypassing an aortic aneurysm encompassing the junction of the aorta and the iliac arteries.

In describing the preferred embodiments of the invention, a balloon deployed stent (such as the Palmaz stent) is described as the device for securing the graft in the vasculature. The invention, however, is not limited to any particular type of stent and other stents (including but not limited to self-expanding stents such as the Walsten stent and stents made of shape memory alloys, e.g. Nitinol) can also be used. In place of a balloon, mechanical deployment means may be used.

In the following description and claims, the terms used have the definitions set forth in U.S. Pat. No. 5,507,769. Specifically, the terms "distal" and "proximal" refer to the device itself and not to the vasculature. The vasculature is referred to with respect to the cephalic (closer to head) and caudal (further from head) directions. The term "above" refers to the regions cephalic of the aneurysm (for example) and "below" refers to the region of the vasculature caudal of the aneurysm.

In the illustrated embodiments, the grafts are cut to the desired length by means of a sharp cutting edge, however, it is conceivable that other types of devices may be used (for example, heat or light responsive devices) to sever the graft. Accordingly, as used herein, the term "cutting" is intended to encompass any procedure for forming a graft to a predetermined length.

Figure 1:
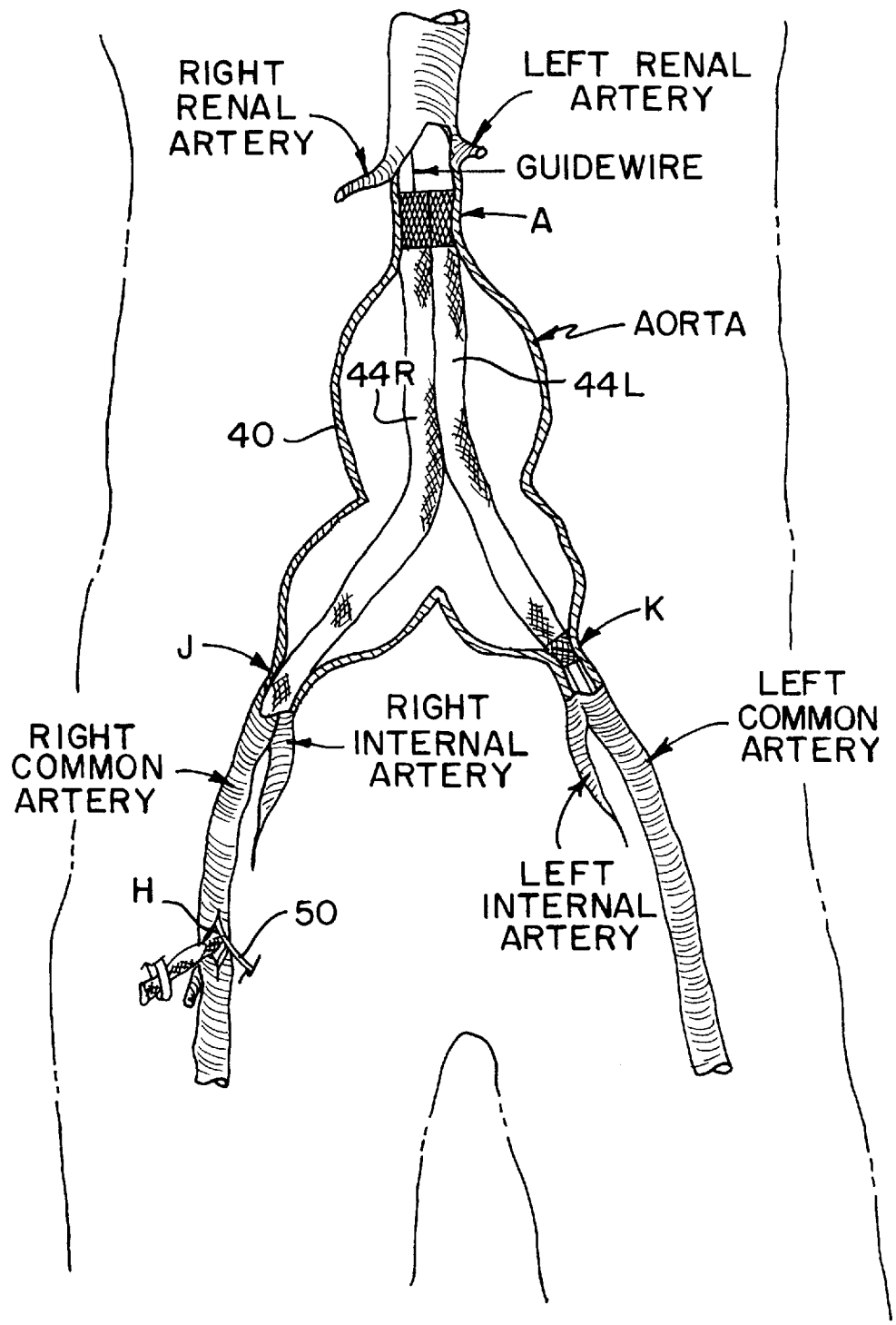
FIG. 1 is a diagrammatic view of a portion of a human vascular system depicting an abdominal aortic aneurysm and demonstrating the way in which the invention is used.

FIG. 1 is a diagram of the arterial system in the vicinity of the abdominal aorta. The aorta, left and right common iliac arteries, left and right renal arteries, and left and right internal iliac arteries are labelled accordingly on the drawing. An aortic aneurysm 40 is shown occupying a large area at the junction of the aorta and the iliac arteries.

To bypass the aneurysm 40 it is necessary that the graft extend from a position caudal of the renal arteries to positions cephalic of the internal iliac arteries so that blood flow through the latter arteries is not interfered with. In practice it is difficult to estimate accurately the proper length of the graft to achieve this objective since the aneurysm may change shape and configuration once pressure has been eliminated from the lumen.

In accordance with the invention, a graft of a defined length, which is expected to be longer than required, is used for each leg. For example, each of the grafts may be approximately 40 cm long but otherwise identical in construction to known grafts as described in U.S. Pat. No. 5,507,769. In the illustrated embodiment, the femoral arteries are entered within the thigh by an arterial incision where the artery is exposed where it comes close to the surface of the skin. A guide wire and catheter are then introduced into the patient's artery and snaked into position above the aneurysm 40. After the left and right guide wires are in place, the grafts 44L and 44R are introduced into the guide catheter and snaked through the aneurysm until their distal ends are properly positioned above the aneurysm. Stents are then deployed to attach the distal ends of the grafts to the aorta near the renal arteries.

The process and apparatus for positioning the distal ends of the grafts and deploying the cephalic stents is fully described in U.S. Pat. No. 5,507,769 and, therefore, is not repeated herein.

The length of the grafts is such that the proximal ends extend from the arterial incision through which the grafts were introduced into the patient's vasculature. A special intraluminal cutting device is provided which may be positioned on the graft extending from the incision. The cutting device is then advanced through the artery over the graft cephalad to a position where it can be actuated to cut the graft to the desired length. The position of the cutting device within the artery is determined by means of an arteriogram. The contrast material for the arteriogram may be injected through a suitable tube attached to the intraluminal cutting device which is accessible to medical personnel. When the arteriogram indicates that the cutting device is in a proper position cephalic of the internal iliac artery, the device is actuated to sever the graft. The proximal end of the graft is then secured to the arterial wall with another stent after the severed portion of the graft and the cutting device have been removed.

In the illustrated example, the same process may be repeated on the opposite side to complete the bifurcated configuration and construct a graft of appropriate length. The invention enables a graft to be formed in which one limb is longer than the other if this is dictated by the arterial anatomy.

FIG. 2 helps to illustrate the way in which various different types of graft cutting devices can be used in accordance with the invention. Continuing with the example of U.S. Pat. No. 5,507,769, FIG. 2 shows the right femoral artery after the graft 44R has been inserted and the cephalic stent deployed to hold the graft in place. The graft 44R extends from an incision H through which the graft was previously inserted as explained in U.S. Pat. No. 5,507,769. The invention provides a way for cutting graft 44R just cephalic of the right iliac artery so that the caudal stent (not shown) can be deployed in the vicinity of attachment point J.

In this embodiment, and as shown more clearly in FIG. 3, the cutting device includes a catheter 50 and an elongated wire 52, in the shape of a snare, which terminates in proximal knobs 54 and 56 and includes a distal cutting loop 58 extending from the distal end of the catheter 50. Attached to the catheter 50 is a small tube 60 having apertures 62 at its distal end so that a contrast solution can be injected into the artery.

The ends of the snare 52 extend through a hemostatic valve 64 which includes a port 66 through which contrast solution can be introduced into the tube 60.

The loop 58 includes a cutting surface 68 (FIG. 4) so that when the snare 52 is pulled tight, the cutting edge 68 will sever the graft 44R. As shown in FIG. 3, the loop 58 extends at an angle from the catheter 50 at its distal end. This angle is selected primarily with the view of enhancing cutting efficiency and minimizing the profile. An angle of 45° appears optimal.

The device shown in FIGS. 1–6 is used as follows.

With the graft 44R extending from the incision H in the femoral artery, the proximal end of the graft is placed through the loop 58. By pulling on one of the knobs 54, 56 and pushing on the other, the sharp cutting edge 68 can be positioned within the catheter 50 (shown in FIG. 3). Using the graft 44R in the fashion of a guide wire, the surgeon then pushes the catheter 50 through the artery with the object of positioning the cutting device cephalic of the right iliac artery. Contrast solution is introduced through port 66, exiting from the holes 62 in tube 60. When the distal end of catheter 50 is positioned cephalic of the right iliac artery, the knobs 54, 56 are manipulated to bring the sharp cutting edge around the graft 44R. The surgeon then grasps the knobs 54 and 56, while maintaining the graft and catheter 50 are stationery, and pulls the loop 58 into the catheter, as shown in FIG. 6. This action, which is analogous to the action of a surgical snare, causes the cutting edge 68 in the loop to sever the graft.

The severed portion of the graft 44R and the catheter 50 are then removed leaving only the guidewire (not shown) extending through the graft. A stent loaded catheter (which may be conventional) is then passed over the guidewire into the graft. When the stent is properly positioned at the caudal end of the graft (as indicated by the radiopaque markers), the stent is deployed and the catheter and guidewire removed. Obviously, the type of stent and its method of deployment form no part of this invention.

In the embodiment of FIGS. 7 and 8, the cutting device comprises two separate wire loops 70 and 72 which are controllable from a position external of the patient. The loop 70 includes a sharp outer cutting edge 70A while the loop 72 includes a sharp inner cutting edge 72A. The graft 44R passes between the two cutting edges 70A and 72A as shown in FIG. 8. The operation of this device is similar to the operation of the device shown in FIGS. 2–6 insofar as positioning the cutting surfaces is concerned. When the devices is properly positioned, the surgeon pulls on the loops 70 and 72 closing the gap between the cutting edges 70A and 72A to sever the graft.

Figure 9:
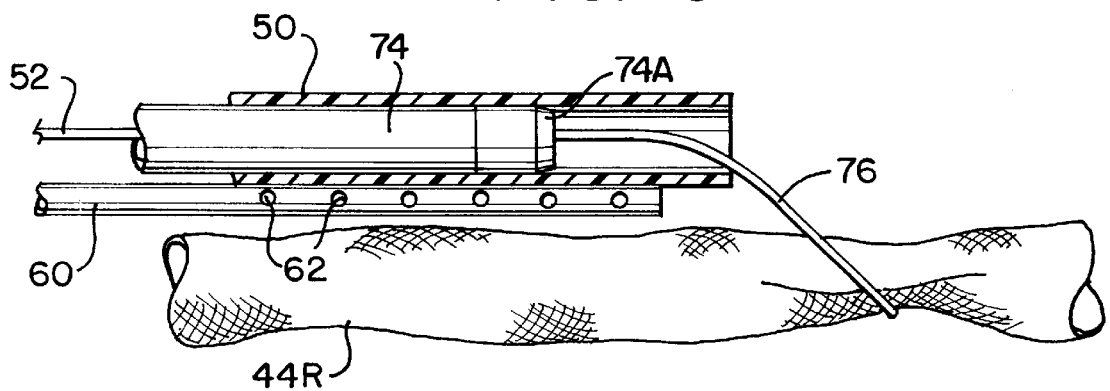
FIG. 9 is a side planar view partially in section showing a third type of cutting device which can be used in accordance with the invention.
Figure 10:
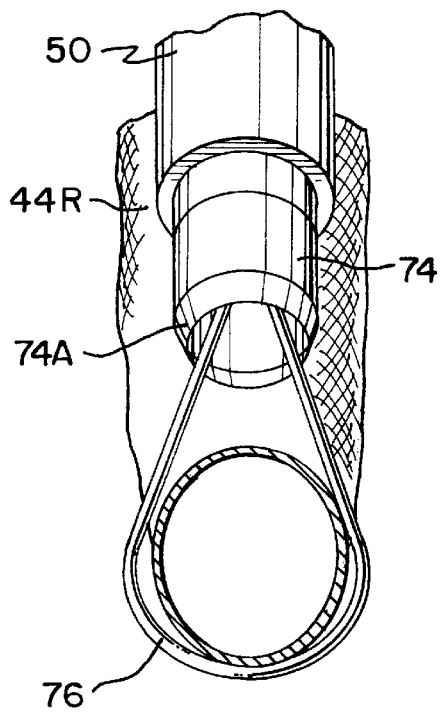
FIG. 10 is a top plan view partially in section showing the cutting device of FIG. 9.
Figure 14:
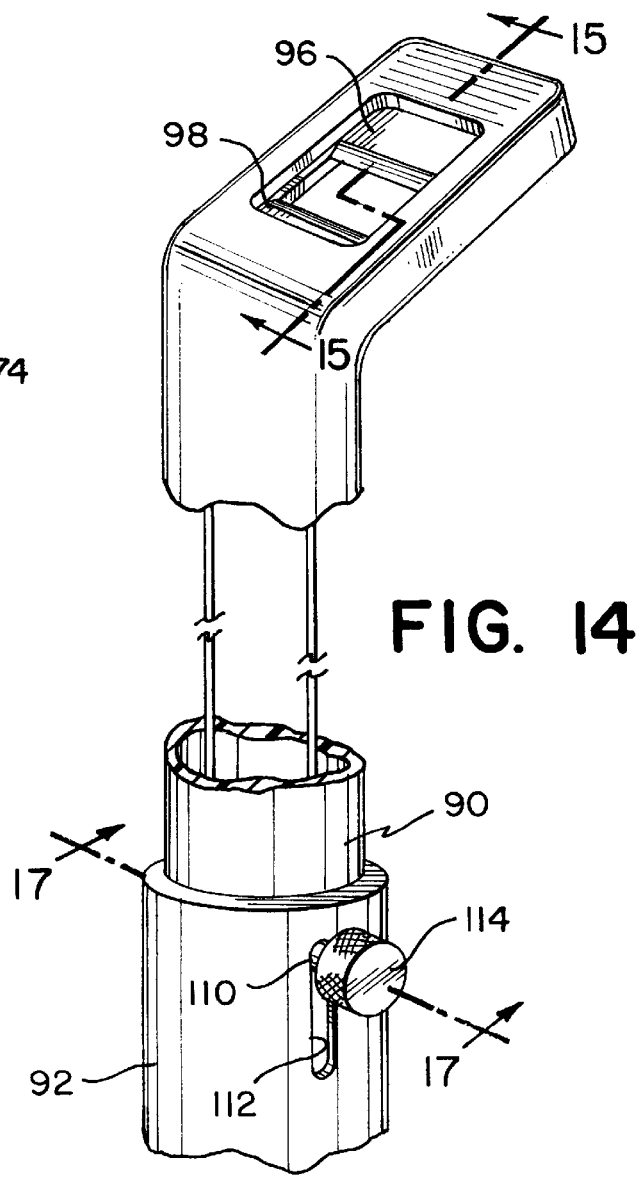
FIG. 14 is perspective view of a fifth type of cutting device which can be used in accordance with the invention.

The cutting device shown in FIGS. 9 and 10 comprises a metallic cylinder 74, which is movable with respect to the catheter 50, and a wire loop 76. The cylinder 74 includes a cutting edge 74A at its distal end. Because of the sharp cutting edge 74A, the cylinder 74 is retracted into catheter 50 as the catheter is moved to the cutting position. When the catheter 50 is properly positioned, the catheter 50 is pulled proximally to the position shown in FIG. 10, exposing cutting edge 74A. The wire loop 76 is then pulled forcing the graft against the cutting surface 74A to sever the graft.

FIGS. 11, 12 and 13 show an embodiment of the invention which can be introduced into the vasculature percutaneously and which requires no additional catheters to deploy the cephalic and caudal stents.

This device comprises a catheter or sheath 80 which envelopes the graft 44R and a balloon catheter 82 which extends through the interior of the graft 44R. The balloon catheter 82 supports proximal and distal balloons 84, 85, 86 and 87. The catheter 82 will include four inflation lumens (not numbered) so that the four balloons can be selectively inflated and deflated.

A caudal stent 88 is mounted on deployment balloon 85 and a cephalic stent 91 is mounted on the deployment balloon 87. As is conventional, the distal end of the graft 44R is attached to the cephalic stent 91, for example, by sewing.

As best shown in FIG. 13, the cutting device in this case comprises a circular blade 89 mounted for rotation within sheath 80. The proximal balloon 84 when expanded, pushes the graft 44R into contact with the blade 89 so that the graft can be cut as described below.

As indicated above, an advantage of this embodiment is that it can be introduced percutaneously into the patient's vasculature. Accordingly, in using the embodiment of FIGS. 11–13, after the guidewire is in position, the entire assembly including the graft/stent complex, balloon catheter 82 and sheath 80 are advanced along the guidewire until the cephalic stent 91 is properly positioned, as indicated by contrast solution. The guide sheath 80 is then retracted to expose the stent 91 which is deployed by expanding balloon 87, thus pinning the distal end of the graft. Deployment balloon 87 is next deflated and the balloon catheter 82 and sheath 80 retracted. The catheter 82 is retracted until the distal end of the sheath 80 is positioned just below the attachment point J. This is determined by means of the contrast solution introduced through tube 60 as in the previous embodiments.

The balloon catheter 80 is then retracted through the graft 44R until the balloon 84 is positioned in the distal end of the sheath 80 as shown in FIG. 12. Proper positioning can be assured by external markings on the balloon catheter which are visible to the surgeon. With the balloon catheter 82 in position, the balloons 84 and 86 are inflated. The expanded distal balloon 86 holds the graft 44R in position so that it does not retract after the graft has been cut to size. (In place of a balloon 84, a solid material may be employed to serve as an anvil for the cutting blade.) The proximal balloon 84 forces the graft against the circular blade 89. The guide sheath 80 is then rotated from its proximal end causing the circular blade 89 to form an annular cut in graft 44R in the desired location. Balloons 84 and 86 are then deflated and the severed proximal portion of graft 44R removed, through the incision H. The stent 88 may be then be deployed by expanding the balloon 85 beneath the stent in conventional fashion. The balloon catheter 82 and guide sheath 80 are then removed, leaving the graft in place pinned by both the cephalic and caudal stents as desired.

FIGS. 14–17 illustrate a "guillotine" type of cutting arrangement which would be used in much the same way as the embodiments of FIGS. 2–10, i.e. with the cutting device encircling the graft. In this embodiment, a catheter 90 is supported in a base 92 at its proximal end and terminates in a head 94 at its distal end which contains the cutting mechanism. The cutting mechanism comprises a fixed blade 96 secured to head 94 and a movable blade 98 which is biased by a pair of return springs 100 to its open position. The movable blade 98 is operated by a pair of pull cables 102 which extend from the base 92 through the catheter 90 into the head 94. The head includes horizontally arrayed pulleys 104 at its distal end and vertically arrayed pulleys 106 at its proximal end. Each of the pull cables 102 passes over a vertically arrayed pulley 106, around a horizontal pulley 104, and through a return spring 100 and a suitable bore (not numbered) within the movable blade 98. Each cable is anchored in conventional fashion at the proximal end of the blade 98 (FIG. 16).

As shown in FIG. 17, the proximal ends of the pull cables 102 are attached to a pin 110 which slides in slots 112 within the base 92. Pin 110 terminates in control knobs 114 which are accessible to the surgeon. The surgeon, by pushing the control knob 114 proximally against the force of a return spring 116 exerts a force on the movable blade 98 which will pull it toward the fixed blade 96 to sever a graft which is positioned between the blades.

A sixth type of cutting device is shown in FIG. 18. This device is an iris type cutter which includes a series of blades 120 which may be movable in much the same way as the iris of a camera. Movement of the blades 120 is controlled by a rotatable knob 122 at the proximal end of the catheter through an elongated rod 124 and a suitable transmission (not shown). The iris blades 120 may also be actuated by means of pull wires.

It is contemplated that the cutting device will be packaged as part of an overall system. In such a case, the cutting device will be introduced with the graft, with the stent deploying catheter inside the graft as is customary. After the cephalic stent is deployed, the stent deployment catheter can be removed and the cutting device positioned to cut the caudal end of the graft. In this arrangement, it is likely, though not necessary, that the cutting device will be positioned by pulling on the catheter 50, which is generally preferable to pushing although both arrangement are contemplated by the invention.

The invention contemplates the use of any type of cutting mechanism besides those illustrated in this specification for the purpose of cutting a graft to size after it has been situated in the vasculature. Furthermore, although the invention has been described in the context as U.S. Pat. No. 5,507,769, it is anticipate and intended that the invention will be used in any situation where a graft may be used.

What is claimed is:

1. A device for endoluminally cutting a graft having a wall between inner and outer surfaces thereof, comprising:

an elongated catheter having cutting means remote from its proximal end for cutting through the wall of the graft to sever the graft endoluminally to a desired length, said cutting means including a portion shaped so that the catheter can be positioned relative to the graft with the graft in close proximity to the cutting means, and actuator means at the proximal end of the catheter for actuating said cutting means to sever the graft endoluminally.

2. A device according to claim 1, wherein said cutting means is angularly disposed with respect to said catheter, the angle being greater than 90°.

3. A device according to claim 2, wherein the catheter is positioned outside of said graft.

4. A device according to claim 1, further including a tubular member for injecting a contrast solution in the vicinity of a distal end of said catheter.

5. A device according to claim 1, further comprising:

a guide sheath, a graft disposed within said guide sheath, cephalic and caudal stents releasably mounted to said catheter, and means for deploying said stents coaxial with said stents.

6. A device according to claim 5, wherein said stent deployment means includes a means for urging a portion of said graft against said cutting means.

7. A device according to claim 6, wherein said cutting means is actuable by rotating said guide sheath.

8. A device according to claim 6, wherein said means for urging comprises a selectively expandable balloon.

9. A device according to claim 6, including an expandable balloon mounted on said catheter between said cephalic and caudal stents, said balloon being expandable so as to engage said graft when said cutting means is actuated.

10. A device according to claim 1, wherein said portion is a snare, said snare being advanced over the graft and movable relative to said catheter.

11. A device according to claim 1, further comprising a graft.

12. A device for endoluminally cutting a graft, comprising an elongated catheter having cutting means remote from its proximal end, said cutting means including a portion shaped so that the catheter can be advanced along the graft with the graft in close proximity to the cutting means, and actuator means at the proximal end of the catheter for actuating said cutting means to sever the graft endoluminally, wherein said catheter and graft are coaxial, the catheter enveloping said graft.

13. A device according to claim 12, including a balloon catheter coaxial with said catheter and said graft, the balloon catheter being inside said graft and including means for supporting the graft so that it can be severed.

14. A device according to claim 13, wherein the catheter enveloping the graft includes a cutting blade and is rotatable to sever said graft.

15. A device according to claim 12, further comprising a graft.

* * * * *

UNITED STATES PATENT AND TRADEMARK OFFICE
CERTIFICATE OF CORRECTION

PATENT NO.   : 5,827,310
DATED        : OCTOBER 27, 1998
INVENTOR(S)  : Michael MARIN et al.

It is certified that error appears in the above-identified patent and that said Letters Patent is hereby corrected as shown below:

On the title page,

Item [54]   The title of the patent is incorrect.
            The correct title should be
            METHOD FOR FORMING CUSTOM LENGTH GRAFTS
            AFTER ENDOLUMINAL INSERTION Item [73]   The address of the Assignee is incorrect.
            The correct address should be TERAMED, INC.,
            ST. PAUL MINNESOTA, 55108

Signed and Sealed this

Eighteenth Day of May, 1999

Attest:

Q. TODD DICKINSON

*Attesting Officer*    *Acting Commissioner of Patents and Trademarks*